(12) United States Patent
Kim et al.

(10) Patent No.: US 10,639,261 B2
(45) Date of Patent: May 5, 2020

(54) METHOD FOR PREPARING 3,6-ANHYDRO-L-GALACTOSE, AND USE THEREOF

(71) Applicant: Korea University Research and Business Foundation, Seoul (KR)

(72) Inventors: Kyoung Heon Kim, Seoul (KR); In Geol Choi, Seoul (KR); Nam Joo Kang, Daegu (KR); Eun-Ju Yun, Seoul (KR); Sae Young Lee, Gyeonggi-do (KR); Ji Hye Kim, Daegu (KR); Young Ah Kim, Daegu (KR); Bo Bae Kim, Daegu (KR); Eun Ji Baek, Daegu (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/100,337

(22) Filed: Aug. 10, 2018

(65) Prior Publication Data

US 2018/0344607 A1 Dec. 6, 2018

Related U.S. Application Data

(62) Division of application No. 15/689,840, filed on Aug. 29, 2017, now Pat. No. 10,071,041, which is a division of application No. 15/352,073, filed on Nov. 15, 2016, now abandoned, which is a division of application No. 14/373,274, filed as application No. PCT/KR2013/000423 on Jan. 18, 2013, now abandoned.

(30) Foreign Application Priority Data

Jan. 18, 2012 (KR) .................. 10-2012-0005716
Jan. 18, 2013 (KR) .................. 10-2013-0005704

(51) Int. Cl.
| | |
|---|---|
| *A61K 31/7004* | (2006.01) |
| *A61K 8/60* | (2006.01) |
| *A61Q 19/02* | (2006.01) |
| *A61Q 19/00* | (2006.01) |
| *C12P 19/14* | (2006.01) |
| *C12P 19/02* | (2006.01) |
| *C07H 1/08* | (2006.01) |
| *C07H 3/10* | (2006.01) |

(52) U.S. Cl.
CPC ............ *A61K 8/60* (2013.01); *A61K 31/7004* (2013.01); *A61Q 19/00* (2013.01); *A61Q 19/007* (2013.01); *A61Q 19/02* (2013.01); *C07H 1/08* (2013.01); *C07H 3/10* (2013.01); *C12P 19/02* (2013.01); *C12P 19/14* (2013.01); *C12Y 302/01* (2013.01)

(58) Field of Classification Search
None
See application file for complete search history.

(56) References Cited

U.S. PATENT DOCUMENTS

| 6,322,814 B1 | 11/2001 | Miller |
| 8,486,654 B2 | 7/2013 | Koo et al. |
| 8,771,996 B2 | 7/2014 | Kim et al. |
| 9,297,000 B2 | 3/2016 | Choi et al. |
| 2003/0105029 A1 | 6/2003 | Enoki et al. |
| 2011/0306059 A1 | 12/2011 | Koo et al. |

FOREIGN PATENT DOCUMENTS

| EA | 1038879 B1 | 9/2000 |
| EP | 1038879 B1 | 9/2000 |
| EP | 1166786 A1 | 2/2002 |
| JP | 1990065788 | 3/1990 |
| JP | 1990065788 A | 3/1990 |
| JP | 2006282675 A | 10/2006 |
| KR | 1020010031895 A | 4/2001 |
| KR | 1020100040438 A | 4/2010 |
| KR | 1020100108241 A | 6/2010 |
| KR | 1020110113287 A | 10/2011 |
| KR | 1020110115905 A | 10/2011 |
| KR | 101087265 B1 | 11/2011 |
| WO | 2010110599 A2 | 9/2010 |

OTHER PUBLICATIONS

An et al., "p-Coumaric acid not only inhibits human tyrosinase activity in vitro but also melanogenesis in cells exposed to UVB," Phytotherapy Research (2010); 24:1175-1180.

Chen et al., "The preparation and bioactivity research of agaro-oligosaccharides," Food Technol. Biotechnol. (2005); I3(1):2-36.

Chirapart et al., "Effects of partial acid hydrolysis on physical and chemical properties of agar from a newly reported Japanse agarophyte (*Gracilariopsis lemaneiformis*).,"Journal of Applied Phycology (1997); 9:73-76.

Dhen et al., "The preparation and bioactivity research of agaro-oligosaccharides," Food Technol. Biotechnol. (2005); I3(1):2-36.

Ducatti et al., "Production of agaro- and carra-oligosaccharides by partial acid hydrolysis of galactans," Brazilian Journa lofPharmacognosy (2011); 21(2):296-304.

Ishihara et al., "Melanostatin, a new melanin synthesis inhibitor. Production, isolation, chemical properties, structure and biological activity," J. Antibiot (Tokyo) (Jan. 1991); 44(1):25-32.

Jol et al., "A novel high-performance anion-exchange chromatographic method for the analysis of carrageenans and agars contianing 3,6-anhydrogalactose," Anal Biochem. (Mar. 15, 1999); 268(2):213-22.

(Continued)

*Primary Examiner* — Traviss C McIntosh, III
(74) *Attorney, Agent, or Firm* — Fox Rothschild LLP

(57) ABSTRACT

The present invention relates to a method for preparing 3,6-anhydro-L-galactose, and use thereof. More specifically, 3,6-anhydro-L-galactose, which is a monosaccharide constituting agar, is produced in a high yield through chemical and enzymatic methods, and the physiological activities thereof such as whitening, moisturizing, antioxidant, anti-inflammatory activities and the like are displayed, thereby enabling industrial use thereof.

2 Claims, 9 Drawing Sheets

Specification includes a Sequence Listing.

(56) References Cited

OTHER PUBLICATIONS

Kim et al., "Overexpression and molecular characterization of Aga50D from *Saccharophagus degradans* 2-40: an exo-type β-agarase producing neoagarobiose," Appl Microbiol Biotechnol (2010); 86:227-234.
Kim et al., "Acidity tunable ionic liquids as catalysts for conversion of agar into mixed sugars.," Bull. Korean Chem. Soc. (2010); 31(2):511-514.
Miller et al., "A 13C N.M.R. study of some disaccharides from algal polysaccharides.," Aust. J. Chem. (1982); 35:853-856.
Munegumi, Toratane, "Where is the Border Line between Strong Acids and Weak Acids?," World Journal of Chemical Education (2013); 1(1):12-16.
Rees, D.A. "Enzymic Synthesis of 3:6-Anhydro-L-Galactose within Porphyran from L-Galactose 6-Sulphate Units," Biochemical Journal (1961); 81:347-352.
Sugano et al., "Purification and characterization of novel enzyme, alpha-neoagarooligosaccharide hydrolase (alpha-NAOS hydrolase), from a marine bacterium, *Vibrio* sp. strain JT0107.," J. Bacteriol. (Nov. 1994); 176 r,22):6812-6818.
Yun et al., "Production of 3,6-anhydro-L-galactose from agarose by agarolytic enzymes of *Saccharophagus degradans* 2-40," Process Biochemistry (2011); 46:88-93.
r.:hirapart et al., "Effects of partial acid hydrolysis on physical and chemical properties of agar from a newly reported Japanse agarophyte (*Gracilariopsis lemaneiformis*).,"Journal of Applied Phycology (1997); 9:73-76.

METHOD FOR PREPARING 3,6-ANHYDRO-L-GALACTOSE, AND USE THEREOF

CROSS-REFERENCE TO RELATED APPLICATION

This application is a Divisional application of U.S. application Ser. No. 15/689,840, filed Aug. 29, 2017, which is a Divisional of U.S. application Ser. No. 15/352,073, filed Nov. 15, 2016, now abandoned, which is a Divisional of U.S. application Ser. No. 14/373,274, filed on Jul. 18, 2014, which is the U.S. National Phase of International Application No. PCT/KR2013/000423, filed on Jan. 18, 2013, which in turn claims priority to 10-2013-0005704 filed Jan. 18, 2013 and Korea Application No. 10-2012-0005716, filed Jan. 18, 2012, the disclosures of which are incorporated herein by reference.

BACKGROUND

1. Field of the Invention

The present invention relates to 3,6-anhydro-L-galactose prepared through chemical and enzymatic methods and industrial use thereof using physiological efficacy.

2. Discussion of Related Art

Agar (or agarose) which is a main polysaccharide constituting a red alga is a polymer in which two monosaccharides, 3,6-anhydro-L-galactose and D-galactose, are alternately bound via α-1,3 linkage and β-1,4 linkage. It has been widely known in that an agarooligosaccharide produced by non-specifically hydrolyzing agarose using a chemical catalyst such as hydrochloric acid, sulfuric acid, and acetic acid exhibits excellent physiological activities such as antioxidant, antiinflammatory, anticancer, whitening, and antiallergic activities. Due to a variety of such physiological activities, agarooligosaccharides and neoagarobiose that are disaccharides have been widely used as functional materials in the fields of food and beauty industries.

As one of monosaccharides constituting the agarooligosaccharides, 3,6-anhydro-L-galactose has problems in that it is produced as a monosaccharide with a very low yield through conventional chemical treatments, and is easily degraded to excessive extents since it has an unstable reducing end and is easily converted into hydroxymethylfurfural in the presence of a high-concentration strong acid under high-temperature reaction conditions (Jol et al (1999) *Anal Biochem.* 268, 213-222, Kim et al (2010) *Bull Korean Soc.* 31(2) 511-514). Also, although the hydrolysis using chemical treatment has an advantage in that it is readily applicable for the purpose of commercialization due to low production cost and simple treatment conditions, it has a problem in that a desired product is produced with a very low yield when specific linkages are broken to obtain the product since the chemical treatment non-specifically breaks the linkages (Chen et al (2005) *Food Technol Biotechnol.* 43(1) 29-36). Further, enzymes specifically breaking linkages in 3,6-anhydro-L-galactose to produce monosaccharides have been reported in recent years, but studies remain to be done to separate, purify, and quantify only 3,6-anhydro-L-galactose from a reaction product.

SUMMARY OF THE INVENTION

Therefore, the present invention is directed to a method for preparing 3,6-anhydro-L-galactose with a high yield through enzymatic degradation while minimizing over-degradation effects caused by chemical treatment.

Also, the present invention is directed to industrial use thereof to investigate the physiological activities of 3,6-anhydro-L-galactose.

According to an aspect of the present invention, there is provided a method for preparing 3,6-anhydro-L-galactose, which includes preparing an agarooligosaccharide by allowing agarose to react with a weak acid at a concentration of 0.5 to 60% (w/v) at a temperature of 40 to 150° C. and a rotary speed of 100 to 200 rpm for 30 minutes to 6 hours, and allowing the agarooligosaccharide to react with an agarose-degrading enzyme and an α-neoagarobiose hydrolase at a temperature of 20 to 40° C. and a rotary speed of 0 to 200 rpm for 30 minutes to 7 days.

In this case, the agarose-degrading enzyme may be an enzyme that breaks a β-1,4-glycosidic linkage between D-galactose and 3,6-anhydro-L-galactose of agarose. More specifically, the agarose-degrading enzyme may be represented by an amino acid sequence set forth in SEQ ID NO: 1.

The neoagarobiose hydrolase may be represented by an amino acid sequence set forth in SEQ ID NO: 3.

According to one exemplary embodiment, the agarose-degrading enzyme and the neoagarobiose hydrolase may be derived from *Saccharophagus degradans* (*S. degradans*) $2\text{-}40^T$.

The method for preparing 3,6-anhydro-L-galactose according to one exemplary embodiment may further include separating and purifying the 3,6-anhydro-L-galactose by sequentially performing adsorption chromatography and gel-permeation chromatography on the 3,6-anhydro-L-galactose.

According to another aspect of the present invention, there is provided a cosmetic composition for skin whitening or moisturizing including 3,6-anhydro-L-galactose.

According to still another aspect of the present invention, there is provided cosmetic use of 3,6-anhydro-L-galactose for skin whitening or moisturizing.

According to still another aspect of the present invention, there is provided a pharmaceutical composition for preventing or treating a skin pigmentation disease including 3,6-anhydro-L-galactose.

According to still another aspect of the present invention, there is provided use of the 3,6-anhydro-L-galactose for preparing the pharmaceutical composition for preventing or treating a skin pigmentation disease.

According to still another aspect of the present invention, there is provided a cosmetic or medical method for whitening or moisturizing a skin of a mammal, preferably, a human, which requires skin whitening or moisturizing. Here, the cosmetic or medical method includes administering an effective amount of 3,6-anhydro-L-galactose, preferably, a pharmaceutical or cosmetic composition including 3,6-anhydro-L-galactose.

According to still another aspect of the present invention, there is provided a cosmetic or medical method for treating a condition, disease, and/or lesion of the skin associated with regulation of pigmentation. Here, the method includes applying a pharmaceutical or cosmetic composition including 3,6-anhydro-L-galactose onto the skin, and the condition, disease, and/or lesion may be locally advanced due to an increase in synthesis of a melanin pigment, and may be at least one selected from the group consisting of chloasma, freckles, lentigo, nevi, pigmentation caused by use of drugs, post-inflammatory pigmentation, and hyperpigmentation occurring on dermatitis.

According to still another aspect of the present invention, there is provided a pharmaceutical composition for preventing or treating an inflammatory disease, which includes 3,6-anhydro-L-galactose.

According to still another aspect of the present invention, there is provided a method for treating an inflammatory disease in an animal. Here, the method includes administering the composition for preventing or treating an inflammatory disease, which includes a pharmaceutically effective amount of 3,6-anhydro-L-galactose, to a subject.

According to yet another aspect of the present invention, there is provided use of 3,6-anhydro-L-galactose to prepare a pharmaceutical composition for preventing or treating an inflammatory disease.

BRIEF DESCRIPTION OF THE DRAWINGS

In FIG. 1, DP represents a degree of polymerization of a polysaccharide.

In FIG. 3, AHG represents 3,6-anhydro-galactose.

In FIG. 7, α-MSH represents an α-melanocyte-stimulating hormone, NAB represents neoagarobiose, and D-AHG and L-AHG represent D- and L-forms of 3,6-anhydrogalactose, respectively.

DETAILED DESCRIPTION OF EXEMPLARY EMBODIMENTS

Hereinafter, exemplary embodiments of the present invention will be described in further detail.

The present invention is directed to a method for preparing 3,6-anhydro-L-galactose, which includes preparing an agarooligosaccharide by allowing agarose to react with a weak acid at a concentration of 0.5 to 60% (w/v) at a temperature of 40 to 150° C. and a rotary speed of 100 to 200 rpm for 30 minutes to 6 hours, and allowing the agarooligosaccharide to react with an agarose-degrading enzyme and an α-neoagarobiose hydrolase at a temperature of 20 to 40° C. and a rotary speed of 0 to 200 rpm for 30 minutes to 7 days.

The method for preparing 3,6-anhydro-L-galactose according to one exemplary embodiment of the present invention is characterized in that agarose is hydrolyzed under mild conditions using a weak acid, an agarooligosaccharide separated from the acid hydrolysate is allowed to react with an exo-type agarose-degrading enzyme producing disaccharides to produce a neoagarobiose, and monosaccharides, galactose and 3,6-anhydro-L-galactose, are produced through additional reaction with an α-neoagarobiose hydrolase.

The 3,6-anhydro-L-galactose may have a structure represented by the following Formula 1:

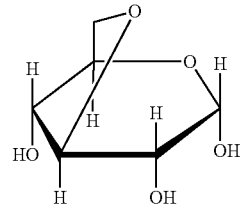

[Formula 1]

Figure 1:
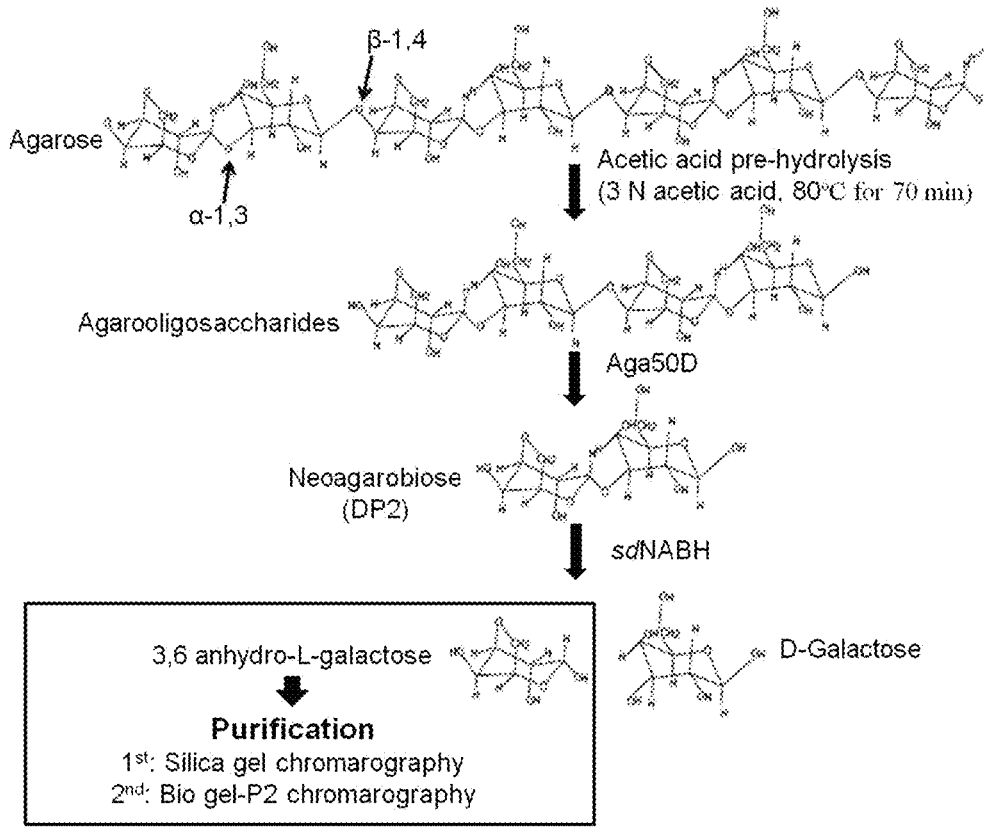
FIG. 1 is a diagram illustrating a procedure of preparing 3,6-anhydro-L-galactose from agarose according to one exemplary embodiment of the present invention.

The method of the present invention will be described in further detail with reference to the procedure of preparing 3,6-anhydro-L-galactose as shown in FIG. 1.

The first step is to prepare an agarooligosaccharide by treating agarose with a weak acid.

The weak acid may be at least one selected from the group consisting of acetic acid, formic acid, succinic acid, citric acid, malic acid, maleic acid, and oxalic acid, which may be used alone or in combination.

The weak acid may be used at a concentration of 0.5 to 60% (w/v) in consideration of the unit production cost of and separation of salts produced after neutralization of weak acid. More specifically, the weak acid may be used at a concentration of 20 to 40% (w/v).

The reaction of the weak acid with the agarose may be performed at a temperature of 40 to 150° C. and a rotary speed of 100 to 200 rpm for 30 minutes to 6 hours. Within these ranges, formation of over-degradation products of agarose by the weak acid may be minimized.

The reaction product obtained after the reaction is an agarooligosaccharide which may be washed to remove the over-degradation product with the residual weak acid, and dried so that the agarooligosaccharide can be obtained in a powdery form.

As the washing solvent, a lower alcohol having 1 to 6 carbon atoms may be used, but the present invention is not limited thereto.

The second step is to prepare 3,6-anhydro-L-galactose by enzymatic degradation of the agarooligosaccharide. Here, the enzymatic degradation is performed by producing a disaccharide, neoagarobiose, by treating the agarooligosaccharide with an exo-type agarose-degrading enzyme and degrading the neoagarobiose into D-galactose and 3,6-anhydro-L-galactose by treating the neoagarobiose with an α-neoagarobiose hydrolase.

The enzymatic reaction may be performed at a temperature of 20 to 40° C. and a rotary speed of 0 to 200 rpm for 30 minutes to 7 days.

The enzymatic reaction will be described in further detail, as follows.

First, an enzyme breaking a β-1,4-glycosidic linkage between D-galactose and 3,6-anhydro-L-galactose of agarose (hereinafter referred to as 'Aga50D') may be used as the agarose-degrading enzyme degrading the agarooligosaccharide to produce the disaccharide, neoagarobiose.

The agarose-degrading enzyme may include an amino acid sequence set forth in SEQ ID NO: 1, and amino acid sequences having sequence identities of 80% or more, 85% or more, 90% or more, 93% or more, 94% or more, 95% or more, 96% or more, 97% or more, 98% or more, and 99% or more with respect to the amino acid sequence.

In the present invention, a polypeptide having a sequence identity of certain percentage (for example, 80%, 85%, 90%, 95%, or 99%) with respect to another sequence means that two sequences has the same amino acid residues at any percentage upon sequence comparison when the sequences are aligned to each other. The alignment and percentage homology or identity may be determined using any proper software program known in the related art, for example, those described in CURRENT PROTOCOLS IN MOLECULAR BIOLOGY (F. M. Ausubel, et al., (eds) 1987 Supplement 30 section 7.7.18). A preferred program includes GCG Pileup programs, for example FASTA (Pearson, et al., 1988 Proc. Natl. Acad. Sci. USA 85: 2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25: 3389-3402). Another preferred alignment program is ALIGN Plus (Scientific and Educational Software, PA), which preferably uses basic parameters. Still another preferred sequence software program which may be used herein is a TFASTA Data Searching program available for Sequence Software Package Version 6.0 (Genetics Computer Group, University of Wisconsin, Madison Wis.).

In this specification, the terms "protein" and "polypeptide" may be used interchangeably. In this specification, one-letter or three-letter codes for amino acid residues are typically used herein.

The enzyme may be derived from S. degradans, but the present invention is not limited thereto.

The enzyme may be transcribed and translated through a coding gene, that is, a DNA fragment which is associated with production of a polypeptide including regions upstream and downstream of a coding region of the enzyme and an intervening sequence between individual coding fragments. For example, the enzyme may have a sequence set forth in SEQ ID NO: 2, but the present invention is not limited thereto.

The agarose-degrading enzyme according to one exemplary embodiment of the present invention may be separated and purified from a supernatant of the S. degradans culture broth, and may be produced and separated in the strains other than S. degradans using a genetic recombination technique or an artificial chemical synthesis method.

When the recombination technique is used, factors used to facilitate expression of typical recombinant proteins, for example, antibiotic-resistant genes, and reporter proteins or peptides usable for affinity column chromatography may be used herein. Such a technique falls within a category which can be easily carried out by those skilled in the art to which the present invention belongs. Also, a supernatant of the S. degradans culture broth may be used instead of the agarose-degrading enzyme according to one exemplary embodiment of the present invention, or a supernatant of a culture broth of an edible strain, for example, a transformed yeast strain obtained by transforming a yeast strain, may be used instead of the agarose-degrading enzyme.

In the present invention, the term "recombination" used in connection with cells, nucleic acids, proteins, or vectors means that the cells, nucleic acids, proteins, or vectors are modified by introduction of heterogeneous nucleic acids or proteins or alteration of innate nucleic acids or proteins, or that the cells are derived from such modified cells. That is, the recombinant cells, for example, express genes which are not found in the cells in an original non-recombinant form, or express original genes which are expressed abnormally upon expression or not expressed at all.

In this specification, the term "nucleic acid" encompasses all kinds of single- or double-stranded DNAs, RNAs, and chemical variants thereof. The terms "nucleic acid" and "polynucleotide" may be used interchangeably herein. Since the genetic codes are degenerated, one or more codons may be used to encode one certain amino acid, and the present invention covers polynucleotides encoding certain amino acid sequences.

The term "introduction" used to insert a nucleic acid sequence into cells refers to "transfection," "transformation," or "transduction," and encompasses reference to integration of a nucleic acid sequence into eucaryotic or procaryotic cells. In this case, the nucleic acid sequence is integrated into the genome (for example, a chromosome, a plasmid, a chromatophore, or mitochondrial DNA) of a cell, and converted into an autonomous replicon or expressed temporally.

The reaction of the agarooligosaccharide with the agarose-degrading enzyme may be performed at a temperature of 20 to 40° C. and a rotary speed of 0 to 200 rpm for 30 minutes to 7 days. More specifically, such a reaction may be performed at a temperature of 25 to 35° C. and a rotary speed of 100 to 150 rpm for 1 to 4 days.

When the agarooligosaccharide is in a powdery form, the agarooligosaccharide may be dissolved in a conventional buffer solution to be used, but the present invention is not limited thereto.

Next, the neoagarobiose hydrolase that can degrade the neoagarobiose produced through the enzymatic reaction into D-galactose and 3,6-anhydro-L-galactose may be a protein having an amino acid sequence set forth in SEQ ID NO: 3 and a mutant protein having at least one substitution, deletion, translocation, and addition in the enzyme. Proteins having the neoagarobiose-hydrolytic activities are also included in a category of the enzymes according to one exemplary embodiment of the present invention, and, preferably, has an amino acid sequence having a sequence identity of 80% or more, 85% or more, 90% or more, 93% or more, 94% or more, 95% or more, 96% or more, 97% or more, 98% or more, and 99% or more with respect to the amino acid sequence set forth in SEQ ID NO: 3 (hereinafter referred to as 'SdNABH').

The enzyme may be derived from S. degradans 2-40, but the present invention is not limited thereto.

The enzyme may be transcribed and translated through a coding gene, that is, a DNA fragment which is associated with production of a polypeptide including regions upstream and downstream of a coding region of the enzyme and an intervening sequence between individual coding fragments. For example, the enzyme may have a sequence set forth in SEQ ID NO: 4, but the present invention is not limited thereto.

The neoagarobiose hydrolase may be separated and purified from a supernatant of the S. degradans culture broth, and may be produced and separated in the strains other than S. degradans using a genetic recombination technique or an artificial chemical synthesis method.

When the recombination technique is used, factors used to facilitate expression of typical recombinant proteins, for example, antibiotic-resistant genes, and reporter proteins or peptides usable for affinity column chromatography may be used herein. Such a technique falls within a category which can be easily carried out by those skilled in the art to which the present invention belongs. Also, a supernatant of the S. degradans culture broth may be used instead of the neoagarobiose hydrolase according to one exemplary embodiment of the present invention, or a supernatant of a culture broth of an edible strain, for example, a transformed yeast strain obtained by transforming a yeast strain, may be used instead of the neoagarobiose hydrolase.

The reaction of the neoagarobiose with the neoagarobiose hydrolase may be performed at a temperature of 20 to 40° C. and a rotary speed of 0 to 200 rpm for 30 minutes to 7 days. More specifically, such a reaction may be performed at a temperature of 25 to 35° C. and a rotary speed of 100 to 150 rpm for 1 to 4 days.

Also, the method for preparing 3,6-anhydro-L-galactose according to one exemplary embodiment of the present invention may further include separating and purifying only 3,6-anhydro-L-galactose from the degradation products of neoagarobiose.

The 3,6-anhydro-L-galactose may be separated and purified with a high purity of approximately 96% by sequentially performing silica gel chromatography that is adsorption chromatography and biogel P2 chromatography that is gel-permeation chromatography.

The purified product is subjected to $^1$H-NMR and 2D-heteronuclear single quantum coherence (HSQC) NMR analysis, and $^1$H ppm and $^{13}$C ppm of previously reported 3,6-anhydro-L-galactose may be compared to identify the structure of the purified product.

In the preparation method according to one exemplary embodiment of the present invention, 76 g of the agarooligosaccharide may be produced from 100 g of agarose through chemical hydrolysis, and 37.55 g of the neoagarobiose and 15.21 g of the 3,6-anhydro-L-galactose may be produced using the Aga50D and SdNABH enzymes, respectively. Also, 3.98 g of pure 3,6-anhydro-L-galactose may be purified through a purification procedure using two kinds of chromatographies.

The present invention is also directed to a cosmetic composition for skin whitening or moisturizing including 3,6-anhydro-L-galactose.

Further, the present invention is directed to cosmetic use of 3,6-anhydro-L-galactose for skin whitening or moisturizing.

The 3,6-anhydro-L-galactose has higher whitening activities than arbutin that has been most widely known as a conventional whitening material, and has an effect of inhibiting the expression of tyrosinase, TRP-1, and the like, which are associated with promoting synthesis of melanin, in a concentration-dependent manner.

According to one exemplary embodiment of the present invention, an in vitro tyrosinase activity test shows that the 3,6-anhydro-L-galactose exhibits a whitening effect by inhibiting expression of the enzyme rather than inhibiting the tyrosinase activities.

Also, the 3,6-anhydro-L-galactose has an effect of promoting the expression of a HAS2 protein that is a moisturizing marker associated with the synthesis of hyaluronic acid.

According to one exemplary embodiment of the present invention, the expression of the HAS2 protein may be regulated by various inflammatory signal transduction pathways such as ERK, and AKT. Here, the 3,6-anhydro-L-galactose may increase phosphorylation of ERK and AKT, and the highly phosphorylated ERK and AKT may increase the expression of the HAS2 protein.

The 3,6-anhydro-L-galactose may be used without limitation as long as it may be synthesized, or may be prepared using the method for preparing 3,6-anhydro-L-galactose according to one exemplary embodiment of the present invention.

Based on an effective amount, a cosmetic preparation or cosmetics including the 3,6-anhydro-L-galactose itself or a mixture obtained by mixing a cosmetologically acceptable carrier with the 3,6-anhydro-L-galactose may be provided. In this case, the cosmetic preparation or cosmetics may be prepared into typical emulsified and solubilized formulations. In the emulsified formulation, the cosmetics may include a lotion, a cream, an essence, and the like, and, in the solubilized formulation, the cosmetics may be a toner. Proper formulations of the cosmetics may, for example, be provided in the form of a solution, a gel, a solid or pasty anhydrous product, an emulsion obtained by dispersing an oily phase in a water phase, a suspension, a microemulsion, a microcapsule, a microgranulocyte, or an ionic (liposomal) or non-ionic vesicle dispersing agent, or may also be provided in the form of a cream, a toner, a lotion, a powder, an ointment, a spray, or a conceal stick.

Also, the formulations of the cosmetics may be prepared in the form of a foam or an aerosol composition further including a compressed propellant.

In this case, the method of preparing cosmetics in the above-described form, and the carrier are apparent to those skilled in the art, and thus the specific description of the method of preparing cosmetics is omitted for clarity.

In addition to the 3,6-anhydro-L-galactose according to one exemplary embodiment of the present invention, the cosmetics may include supplemental agents typically used in the field of cosmetology, such as a fat material, an organic solvent, a dissolving agent, a concentrating agent, a gelling agent, a softening agent, an antioxidant, a suspending agent, a stabilizing agent, a foaming agent, an aromatic, a surfactant, water, an ionic or non-ionic emulsifying agent, a filler, a metal ion sequestering and chelating agent, a preservative, a vitamin, a blocking agent, a moisturizing agent, an essential oil, a dye, a pigment, a hydrophilic or lipophilic activating agent, a lipid vesicle, or any other components typically used in cosmetics.

When the 3,6-anhydro-L-galactose is used for foods or as a food additive, the 3,6-anhydro-L-galactose itself may be added, or may be used in connection with other foods or food components. In this case, the 3,6-anhydro-L-galactose may be properly used according to conventional methods. The amount of the mixed active component may be determined according to a purpose of use (prophylaxis, health, or therapeutic treatment). In general, the composition according to one exemplary embodiment of the present invention may be added at a content of 15 wt % or less, preferably 10 wt % or less, based on the total amount of the active component, upon preparation of foods. However, when the 3,6-anhydro-L-galactose is taken in for a long period of time for the purpose of health and hygiene or the purpose of regulation of health, the amount of the mixed active component may be lower than or equal to the above-described content. When the mixed active component has no problems regarding the safety, the active component may also be used within this content range or less.

The present invention is also directed to a pharmaceutical composition for preventing or treating a skin pigmentation disease, which includes 3,6-anhydro-L-galactose.

Also, the present invention is directed to use of the 3,6-anhydro-L-galactose for preparing the pharmaceutical composition for preventing or treating a skin pigmentation disease.

The pharmaceutical composition according to one exemplary embodiment of the present invention may further include a suitable carrier, excipient, and diluent which are typically used to prepare pharmaceutical compositions.

The pharmaceutical composition according to one exemplary embodiment of the present invention may be formulated in the form of external preparations such as a powder, a granule, a tablet, a capsule, a suspension, an emulsion, syrup, and an aerosol, and in the form of a sterile injectable solution according to conventional methods. Preferably, the pharmaceutical composition may be used in the form of a cream, a gel, a patch, a spraying agent, an ointment, a plaster, a lotion, a liniment, a paste, or a cataplasma.

The carrier, excipient, and diluent that may be included in the pharmaceutical composition according to one exemplary embodiment of the present invention may include lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

When formulated, the pharmaceutical composition may be prepared using a diluent or excipient widely used in the related art, such as a filler, an extending agent, a binding agent, a wetting agent, a disintegrating agent, a surfactant, and the like.

A solid preparation for oral administration may include a tablet, a pill, a powder, a granule, a capsule, and the like. Such a solid preparation may be prepared by mixing at least one excipient, for example, starch, calcium carbonate, sucrose, lactose, or gelatin, with the above-described compound. In addition to the simple excipients, lubricants such as magnesium stearate and talc may also be used. A liquid preparation for oral administration may include a suspension, a liquid for internal use, an emulsion, syrup, and the like. In addition to the widely used simple diluents such as water and liquid paraffin, the liquid preparation may include various excipients, for example, a wetting agent, a sweetening agent, an aromatic, a preservative, and the like. A preparation for parenteral administration may include a sterile aqueous solution, a non-aqueous solvent, a suspension, an emulsion, a lyophilized preparation, a suppository, and the like. A vegetable oil such as propylene glycol, polyethylene glycol, or olive oil, or an injectable ester such as ethyl oleate may be used as the non-aqueous solvent and the suspension. Witepsol, Macrogol, Tween 61, cocoa butter, laurin butter, glycerogelatin, and the like may be used as base of the suppository.

The pharmaceutical composition according to one exemplary embodiment of the present invention may be a formulation for external use in the skin which can be applied to the skin. In this case, the pharmaceutical composition may be prepared in the form of a liquid for external use, such as a cream, a gel, a patch, a spraying agent, an ointment, a plaster, a lotion, a liniment, a paste, or a cataplasma, but the present invention is not limited thereto.

A desirable dose of the pharmaceutical composition according to one exemplary embodiment of the present invention may vary according to the conditions and body weight of a patient, the severity of a disease, the type of a drug, and the route and duration of administration, but may be properly chosen by those skilled in the related art. However, the composition according to one exemplary embodiment of the present invention may be administered daily at a dose of 0.0001 to 100 mg/kg, preferably 0.001 to 10 mg/kg, in order to show a desirable medicinal effect. The liquid for external use may be administered once or several times a day. The dosage is not intended to limit the scope of the present invention at any aspects.

Also, the present invention is directed to a cosmetic or medical method for whitening or moisturizing a skin of a mammal, preferably, a human, which requires skin whitening or moisturizing. Here, the cosmetic or medical method includes administering an effective amount of 3,6-anhydro-L-galactose, preferably, a pharmaceutical or cosmetic composition including 3,6-anhydro-L-galactose.

Likewise, the present invention is directed to a cosmetic or medical method for treating a condition, disease, and/or lesion of the skin associated with regulation of pigmentation. Here, the method includes applying a pharmaceutical or cosmetic composition including 3,6-anhydro-L-galactose onto the skin, and the condition, disease, and/or lesion may be locally advanced due to an increase in synthesis of a melanin pigment, and may be at least one selected from the group consisting of chloasma, freckles, lentigo, nevi, pigmentation caused by use of drugs, post-inflammatory pigmentation, and hyperpigmentation occurring on dermatitis.

The application frequency of the pharmaceutical or cosmetic composition including 3,6-anhydro-L-galactose may vary according to the demands of individual subjects. For example, the application frequency is proposed to be ten times a month to a day, preferably four times a week to a day, more preferably three times a week to a day, and the most preferably one or twice a day.

Also, the present invention is directed to use of the 3,6-anhydro-L-galactose for preparing a pharmaceutical or cosmetic composition for treating, caring, and/or dressing the skin, preferably the skin of a face, a neck, a neckline, a hand, an armpit, a groin, an elbow, and/or a knee, and more preferably a local site of a face, a neck, and/or a hand.

Further, the present invention is directed to a pharmaceutical composition for preventing or treating an inflammatory disease, which includes 3,6-anhydro-L-galactose.

Also, the present invention is directed to a method of treating an inflammatory disease in an animal, which includes administering the composition for preventing or treating an inflammatory disease, which includes a pharmaceutically effective amount of 3,6-anhydro-L-galactose, to a subject.

Furthermore, the present invention is directed to use of the 3,6-anhydro-L-galactose for preparing a pharmaceutical composition for preventing or treating an inflammatory disease.

Figure 8:
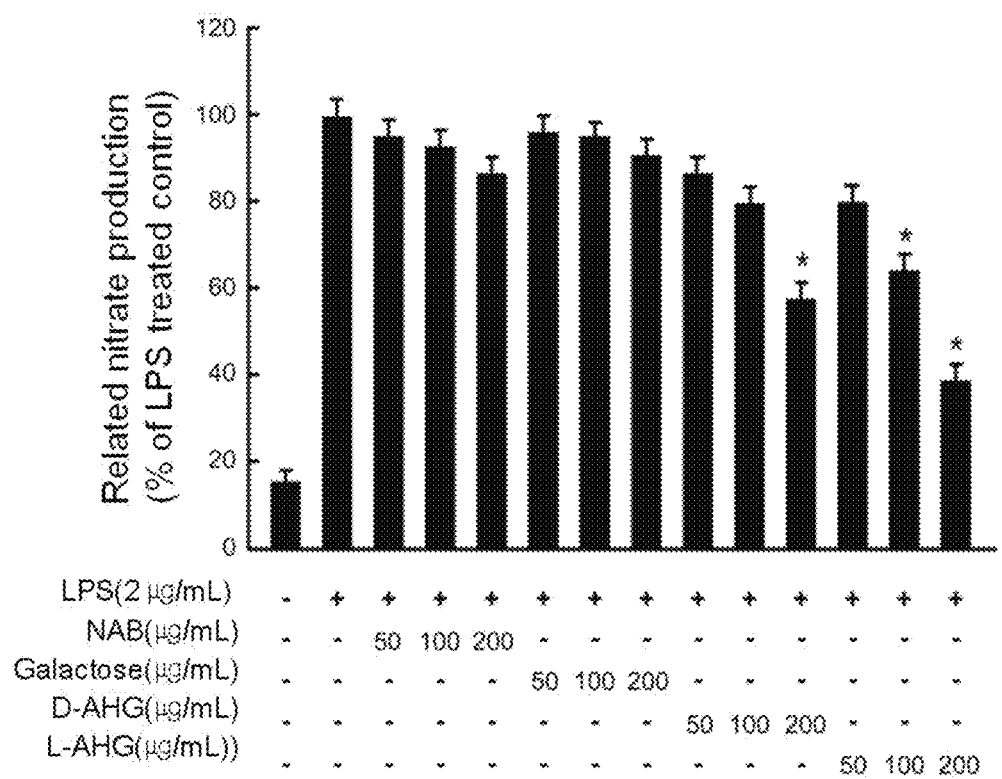
FIG. 8 shows the antioxidant activities of 3,6-anhydro-L-galactose, neoagarobiose, D-galactose, and 3,6-anhydro-D-galactose.

The 3,6-anhydro-L-galactose has an antioxidant activity to inhibit generation of nitrite ($NO_2$), and thus may be used in the pharmaceutical composition for preventing or treating an inflammatory disease since the 3,6-anhydro-L-galactose has the highest antioxidant activity, compared to D-form 3,6-anhydro galactose, and another disaccharide and monosaccharide, such as neoagarobiose and galactose, which constitutes a sea alga (see FIG. 8).

Since the pharmaceutical composition used in the method of treating an inflammatory disease, and the method of administration are described above, the overlapping description of the pharmaceutical composition and the method of administration are omitted for clarity. Meanwhile, the subject to which the pharmaceutical composition for preventing or treating an inflammatory disease may be administered may include all kinds of animals. For example, the subject may be an animal except a human being, including a dog, a cat, a mouse, and the like.

The effective amount of the active component in the pharmaceutical composition means an amount required to treat a disease. Therefore, the effective amount of the active component may be adjusted according to various factors including the kind of a disease, the severity of a disease, the kinds and contents of the active component and other components included in a composition, the kind of a formulation, the age, body weight, general physical condition, gender, and diet of a patient, the time and route of administration, the secretion rate of the composition, the duration of treatment, and drugs used together.

Also, the term "treating" or "treatment" means relieving symptoms, temporally or permanently removing the causes of the symptoms, or alleviating the onset and the progress of, or preventing the illness, disorder, or disease, but the present invention is not limited thereto.

Hereinafter, the present invention will be described in further detail with reference to the following preferred Examples. However, it should be understood that the following Examples are given by way of illustration of the present invention only, and are not intended to limit the scope of the present invention.

<Example 1> Hydrolysis of Agarose Using Acetic Acid

Figure 2:
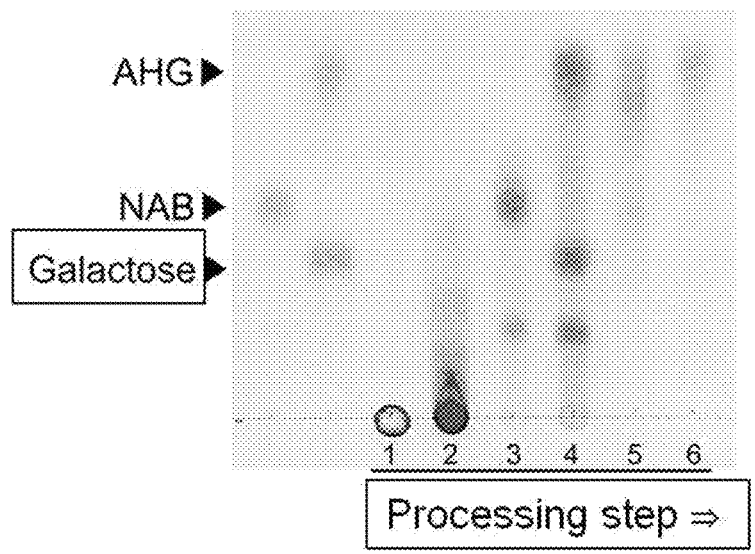
FIG. 2 shows the thin-layer chromatography (TLC) results obtained in a procedure of preparing and purifying 3,6-anhydro-L-galactose from agarose. In the processing step, Lane 1 represents agarose, Lane 2 represents an acetic acid hydrolysate, Lane 3 represents an Aga50D reaction product, Lane 4 represents an SdNABH reaction product, Lane 5 represents 3,6-anhydro-L-galactose separated by silica gel chromatography, Lane 6 represents 3,6-anhydro-L-galactose purified by biogel P2 chromatography, AHG in the Y axis represents 3,6-anhydrogalactose, and NAB represents neoagarobiose.

Agarose that is a representative polysaccharide constituting a sea alga was hydrolyzed with acetic acid. 5% (w/v) of agarose was reacted with 3M acetic acid at 80° C. for 70 minutes and dried to remove acetic acid. Also, acetic acid which remained after drying through a washing procedure using ethanol, and over-degradation products that were able to be produced upon hydrolysis were removed to produce an agarooligosaccharide in the form of a pure powder (FIG. 2).

<Example 2> Production of 3,6-Anhydro-L-Galactose Using Aga50D and SdNABH

To degrade the acid hydrolysate produced in Example 1 into monosaccharides, D-galactose and 3,6-anhydro-L-galactose, the acid hydrolysate was reacted with an exo-type disaccharide-producing enzyme, Aga50D, (see Korean Patent Publication No. 2010-0040438) to produce neoagarobiose as a reaction product.

When the reaction with Aga50D was completed, the Aga50D reaction product was reacted with an SdNABH enzyme (see Korean Patent Publication No. 2010-0108241) in order to produce the monosaccharides, D-galactose and 3,6-anhydro-L-galactose, from the neoagarobiose. The enzymatic reaction conditions were as follows: 5% (w/v) of agarooligosaccharide was dissolved in 100 mL of a 50 mM Tris-HCl buffer solution (pH 7.4), and reacted at 30° C. and 150 rpm for 3 days. The amounts of the enzymes used upon the enzymatic reaction were 10 mg and 2.5 mg for Aga50D and SdNABH, respectively (FIG. 2).

<Example 3> Separation and Purification Using Silica Gel Chromatography and Biogel P2 Chromatography Chromatography was performed to separate and purify only 3,6-anhydro-L-galactose from the reaction products produced in Examples 1 and 2. The reaction products were adsorbed onto celite to form a sample in the form of powder, and subjected to silica gel chromatography that was adsorption chromatography. A solvent obtained by mixing chloroform, methanol, and water at a ratio of 78:20:2 (v/v/v) was used as a mobile phase, and the total volume of the solvent as the mobile phase was 3 L. The volume of one fraction was 20 mL, and the sample composed of a total of 150 fractions was analyzed through TLC. Among these, the fractions containing 3,6-anhydro-L-galactose were collected. Since the biogel P2 chromatography to be further performed separated materials according to the molecular weights, the fractions containing D-galactose having a molecular weight similar to 3,6-anhydro-L-galactose among the fractions containing 3,6-anhydro-L-galactose were excluded (FIG. 3).

Only 3,6-anhydro-L-galactose was able to be purified from the disaccharides and the agarooligosaccharide having a low degree of polymerization with high purity through biogel P2 chromatography. The mobile phase used herein was water, and the volume of one fraction was 2 mL. Among the respective fractions, only the fractions showing spots of 3,6-anhydro-L-galactose on TLC were collected to obtain high-purity 3,6-anhydro-L-galactose (FIG. 2).

As shown in FIG. 2, 76 g of the agarooligosaccharide was produced from 100 g of agarose through chemical hydrolysis in Examples 1 to 3, and 37.55 g of neoagarobiose and 15.21 g of 3,6-anhydro-L-galactose were produced using the Aga50D and SdNABH enzymes, respectively. Also, 3.98 g of the pure 3,6-anhydro-L-galactose was purified through two chromatographies.

Figure 3:
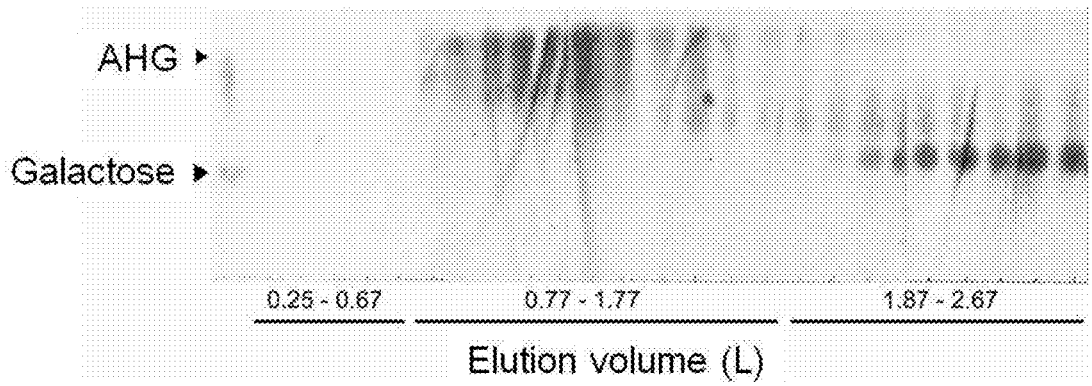
FIG. 3 shows the results of silica gel chromatography-TLC which is the first step of purifying 3,6-anhydro-L-galactose.

Also as shown in FIG. 3, no saccharides were observed in fractions 0.25-067 of elution volume (L), the sugars other than 3,6-anhydro-L-galactose and galactose were observed in fractions 0.77-1.77 (a sample subjected to biogel P2 chromatography after the concentration), and galactose and other sugars were observed in fractions 1.87-2.67.

Figure 4A:
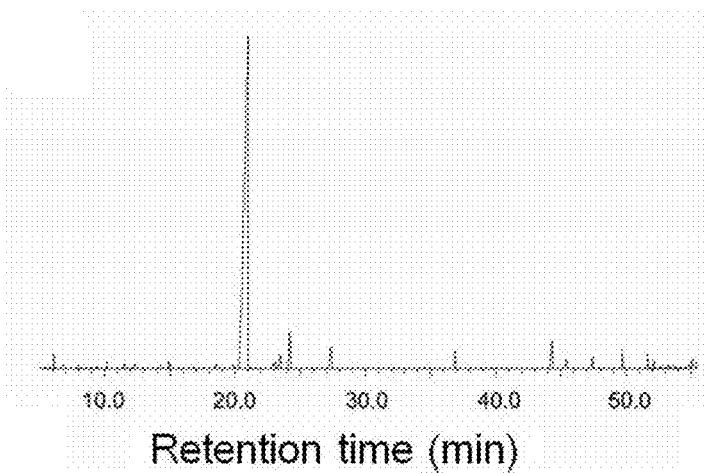
FIG. 4A shows GC/MS total ion chromatograms of a D-form 3,6-anhydro-galactose standard material.
Figure 4B:
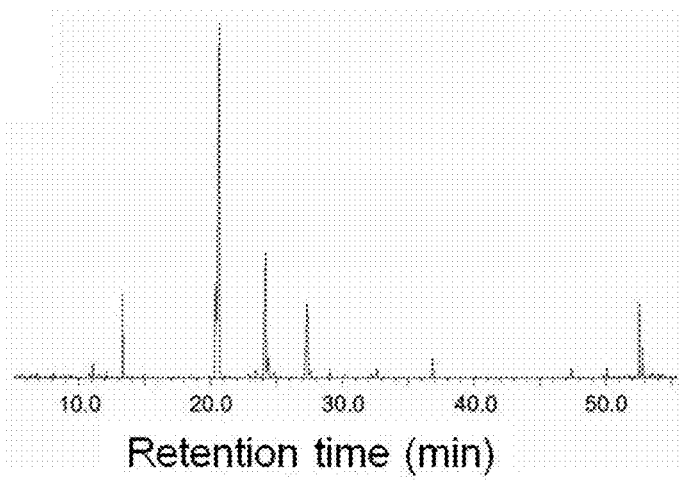
FIG. 4B shows 3,6-anhydro-L-galactose purified according to one exemplary embodiment of the present invention.

<Example 4> Qualification and Quantification of 3,6-Anhydro-L-Galactose Using GC/MS Analysis The high-purity 3,6-anhydro-L-galactose produced in Example 3 was quantified through GC/MS analysis. A derivatization procedure for GC/MS analysis was as follows. The purified sample was dried in a speed-vac, added to 50 μl of 2% (w/v) O-methylhydroxylamine hydrochloride in pyridine, and then reacted at 75° C. for 30 minutes. Then, 80 μl of N-methyl-N-(trimethylsilyl)trifluoroacetamide was added, and reacted at 40° C. and 150 rpm for 30 minutes. The equipment conditions for GC/MS analysis were as follows. A column used for analysis was a DB5-MS capillary column. In the case of the GC column temperature conditions, first, the sample was maintained at a temperature of 100° C. for 3.5 minutes, heated to 160° C., and maintained for 20 minutes. Thereafter, the sample was heated to 200° C., maintained for 15 minutes, finally heated to 280° C., and maintained for 5 minutes. 1 μl of the sample was analyzed at a split ratio of 9.6 (FIG. 4B).

Figure 5:
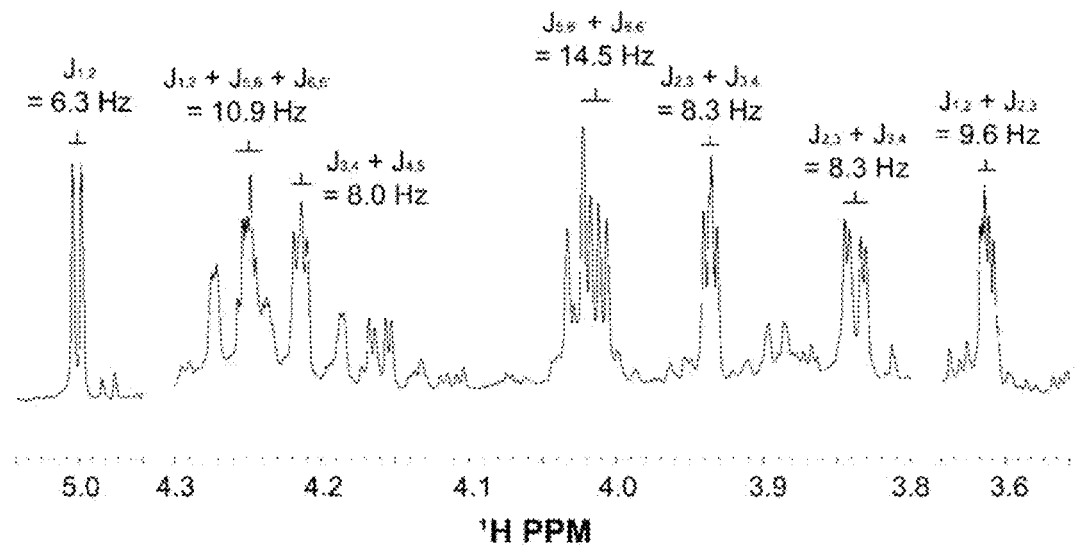
FIG. 5 shows the $^1$H NMR analysis results of 3,6-anhydro-L-galactose separated and purified according to one exemplary embodiment of the present invention.
Figure 6:
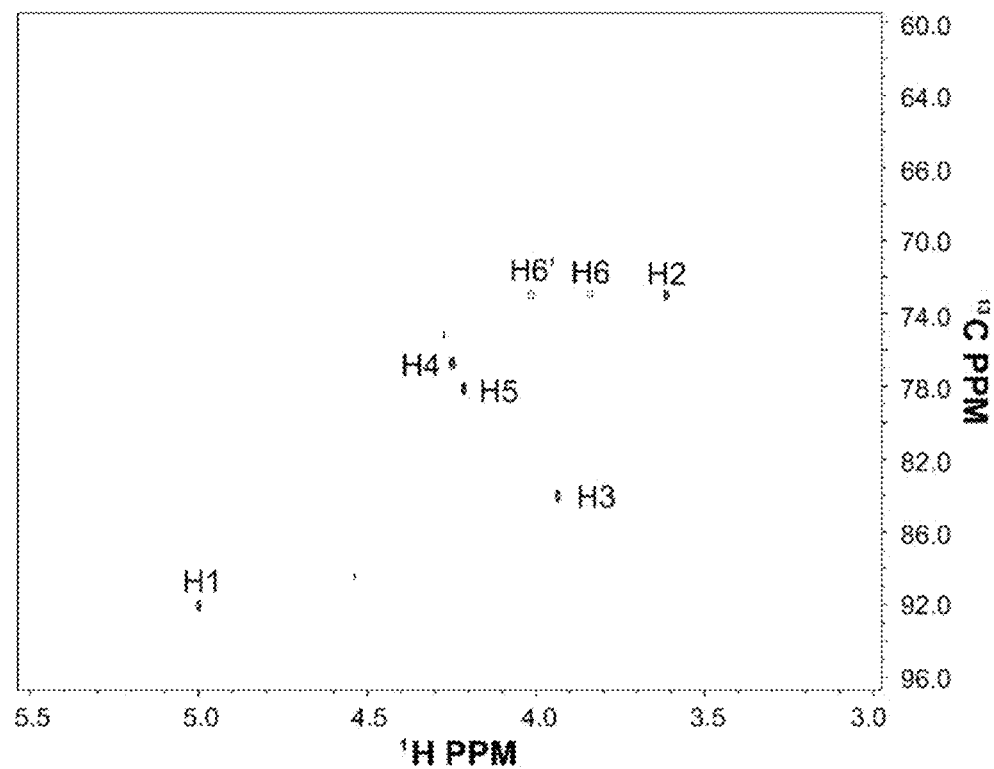
FIG. 6 shows the 2D-HSQC NMR analysis results of 3,6-anhydro-L-galactose separated and purified according to one exemplary embodiment of the present invention.

<Example 5> Identification of Structure of 3,6-Anhydro-L-Galactose Through $^1$H-NMR and 2D HSQC NMR Analyses NMR analyses were performed to identify the chemical structure of the high-purity 3,6-anhydro-L-galactose produced in Examples 1 to 3. 2 mg of a 3,6-anhydro-L-galactose sample was dissolved in $D_2O$, and 3-(trimethylsilyl)-propionic-2,2,3,3-d4 acid was added as the internal standard to calculate the chemical shift. It was confirmed that the chemical structure was identified by comparing the chemical shifts in $^1$H-NMR and 2D HSQC NMR to the resulting values of the previously reported documents (Sugano et al (1994) *J Bacteriol.* 176(22) 6812-6818, Miller et al (1982) *Aust J Chem.* 35(4) 853-856)(FIGS. 5 and 6).

<Example 6> Examination of Whitening and Antioxidant Activities of Separated and Purified 3,6-Anhydro-L-Galactose To determine the whitening activities of the high-purity 3,6-anhydro-L-galactose produced in Examples 1 to 3, the melanoma cells, B16F10, were incubated. Before treatment with α-melanocyte-stimulating hormone that was a hormone promoting the melanin production, the melanoma cells were treated with each of arbutin most widely used as a whitening agent, saccharides (neoagarobiose, D-galactose, and 3,6-anhydro-D-galactose) constituting a red alga, and 3,6-anhydro-L-galactose at concentration of 1, 10, and 100 μg/mL, and the resulting reaction mixture was reacted with the α-melanocyte-stimulating hormone. After the melanoma cells were incubated together for 4 days, the optical densities of the melanoma cells were measured at 475 nm to determine the content of melanin.

Figure 7:
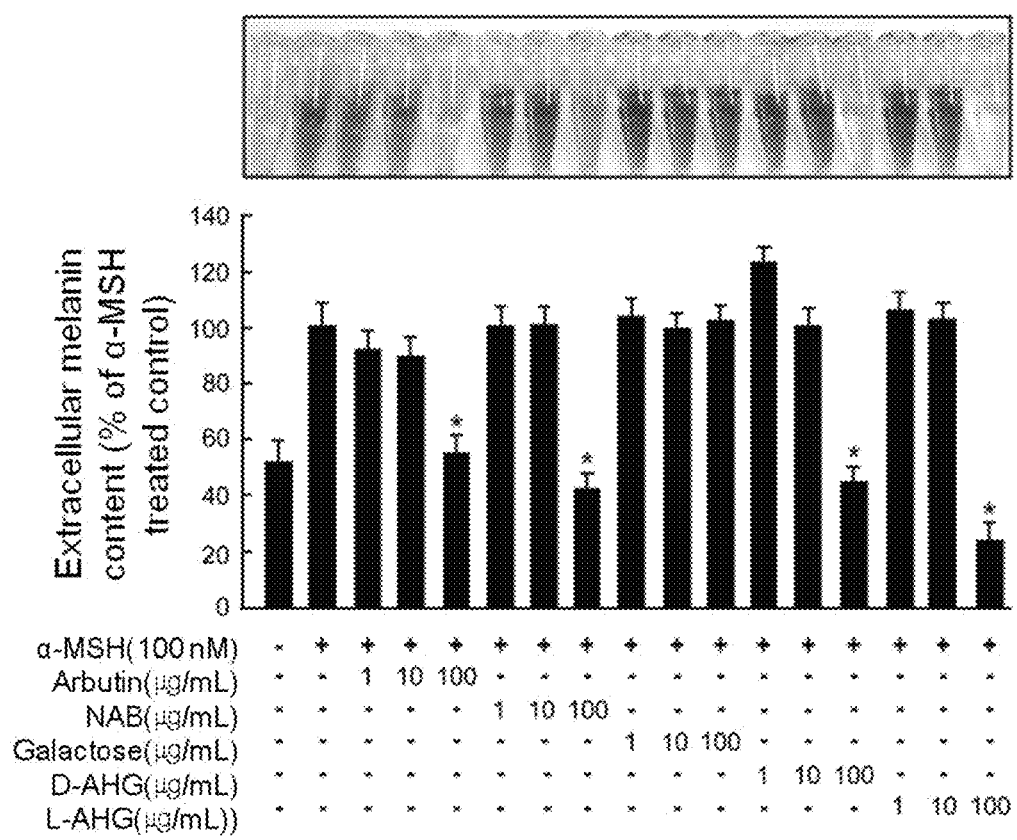
FIG. 7 shows the whitening activities of 3,6-anhydro-L-galactose, neoagarobiose, D-galactose, and 3,6-anhydro-D-galactose.

As a result, it was revealed that the 3,6-anhydro-L-galactose showed very excellent whitening activities, compared to the other treated groups, and, in fact, that the 3,6-anhydro-L-galactose showed higher whitening activities than arbutin which is known as a functional material showing whitening activities (FIG. 7).

<Example 7> Antioxidant Activities of Separated and Purified 3,6-Anhydro-L-Galactose To determine the antioxidant activities of the high-purity 3,6-anhydro-L-galactose produced in Examples 1 to 3, the concentration of nitrite ($NO_2$) in an RAW264.7 cell culture broth was measured by a method using a Griess reaction. The RAW264.7 cells were treated with a lipopolysaccharide at a concentration of 2 μg/mL, and simultaneously treated with each of neoagarobiose, galactose, 3,6-anhydro-D-galactose, and 3,6-anhydro-L-galactose at concentrations of 50, 100, and 200 μg/mL. Thereafter, the RAW264.7 cells were treated together to determine the antioxidant activities. After the RAW264.7 cells were incubated together for 24 hours, the optical densities of the RAW264.7 cells were measured at 540 nm to determine the antioxidant activities.

As a result, it was revealed that the 3,6-anhydro-L-galactose showed very excellent antioxidant activities, compared to the other treated groups, and that the 3,6-anhydro-L-galactose showed higher antioxidant activities than the previously reported 3,6-anhydro-D-galactose (FIG. 8).

<Example 8> Experiment of Whitening Effect of 3,6-Anhydro-L-Galactose in Human Epidermal Melanocytes Melanin is a natural pigment found to give colors to the skin and hair. The known main function of melanin is to protect the skin from DNA damage caused by irradiation of absorbed and scattered ultraviolet rays. However, the formation or abnormal distribution of excessive melanin may cause irregular skin hyperpigmentations such as chloasma, freckles, senile lentigos, and the like. The previous studies showed that the ultraviolet irradiation increases levels of an α-melanocyte-stimulating hormone (α-MSH) and ACTH, and a related receptor thereof, that is, a melanocortin 1 receptor (MC1R) to promote the expression of melanin biosynthesis enzymes including tyrosinase, and tyrosinase-related proteins (TRPs). A copper-containing glycoprotein, tyrosinase, is a rate limiting enzyme which is important for synthesis of melanin in certain cell organs, that is, melanosomes produced only in melanocytes. Therefore, a decrease in tyrosinase expression was considered to be a good strategy for inhibiting the pigmentation of the skin.

Also, TRP-1 is structurally associated with tyrosinase, has an amino acid homology of approximately 40%, and is present in the melanosomes such as tyrosinase. The previous studies reported that the mutations of TRP-1 resulted in pale skin or hair color, which was observed in a certain type of oculocutaneous albinism. Also, it was proposed that TRP-1 played a role in melanin biosynthesis since the inhibition of TRP-1 expression was associated with the hypopigmentation.

Therefore, effects of L-AHG on tyrosinase and TRP-1 expression induced by α-MSH were examined in order to evaluate whether L-AHG had the probability of showing the whitening activities on the skin. Properly pigmented human epidermal melanocytes (HEMs, Cascade Biologics (Oregon, USA)) derived from the neonatal epidermis were used as the cells for this purpose. The cells were cultured at a temperature of 37° C. under a moisturizing environment containing 5% $CO_2$. The culture medium for HEMs was Medium 254 (Cascade Biologics (Oregon, USA)) supplemented with HMGS.

HEMs ($1\times10^5$) were cultured in a 6-cm dish for 24 hours. Before the HEMs were exposed to 100 nM α-MSH (Sigma-Aldrich, St. Louis, Mo., USA) for several days, the cells were treated with 3,6-anhydro-L-galactose (L-AHG) at concentrations of 0, 25, 50, and 100 μg/mL for an hour. Then, the cells were lysed in a lysis buffer [20 mM Tris-HCl (pH 7.5), 150 mM NaCl, 1 mM $Na_2$EDTA, 1 mM EGTA, 1% Triton X-100, 2.5 mM sodium pyrophosphate, 1 mM β-glycerophosphate, 1 mM Na$_3$VO$_4$, 1 g/mL leupeptin, 1 mM phenylmethylsulfonyl fluoride (PMSF), and a protease inhibitor cocktail tablet]. The concentration of the proteins was measured according to the manufacturer's manual using a dye-conjugated protein assay kit (Bio-Rad Laboratories Inc. Hercules, Calif., USA). 10% SDS-PAGE was performed on the lysed proteins (20 to 40 μg), and the lysed proteins were transferred to a polyvinylidene fluoride (PVDF) membrane through electrophoresis (Millipore Corp., Bedford, Mass., USA). After blotting, the membrane was blocked with 5% skim milk (MB cell, Los Angeles, Calif., USA) for 2 hours, and incubated with a primary antibody (goat anti-mouse IgG-HRP) overnight at 4° C. Thereafter, the membrane was incubated with a secondary antibody (a goat anti-rabbit IgG HRP-conjugated secondary antibody), and the antibody-bound proteins were detected using a chemifluorescence detection kit (Amersham Pharmacia Biotech, Piscataway, N.J.). As the control, an expression level of β-actin was measured. The data represented the values obtained from the independent experiments performed in duplicate.

The in vitro tyrosinase analyses were performed using a slight modification of the reported method (Ishihara Y et al., *The journal of antibiotics* (Tokyo) 1991; 44:25-32; An SM, Koh J S, Boo Y C, *Phytotherapy Research* 2010; 24:1175-1180). In brief, 250 μl of a 0.1M potassium phosphate buffer (pH 6.8) was put into a 24-well plate, and 25 μl of a mushroom-derived tyrosinase (2,000 units/mL), 25 μl of a sample, and 225 μl of distilled water were put into each well. The plate was incubated at 25° C. for 10 minutes, and 25 μl of 1 mM L-tyrosine used as a substrate was added to the wells. Then, the plate was incubated at 25° C. for 10 minutes, and the optical density of each well measured at 475 nm using a microplate reader (Sunrise-Basic Tecan, Austria). Each of the measured values was represented by a variation (%) with respect to the control. L-tyrosine was used as the substrate, and arbutin was used as the positive control. The results were represented by the relative tyrosinase activities to the non-treated control.

Figure 9A:
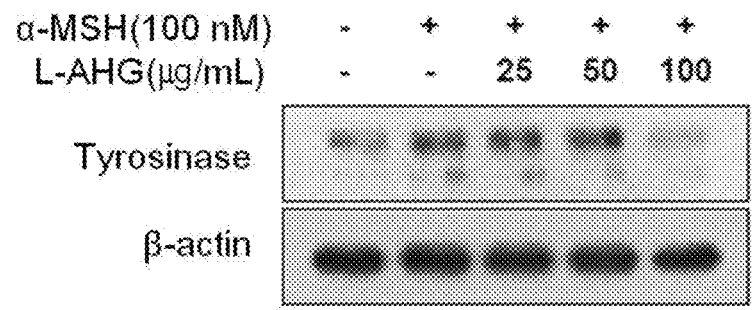
FIG. 9A shows the results of tyrosinase expression in the cells exposed to α-MSH after treatment according to concentrations of L-AHG
Figure 9B:
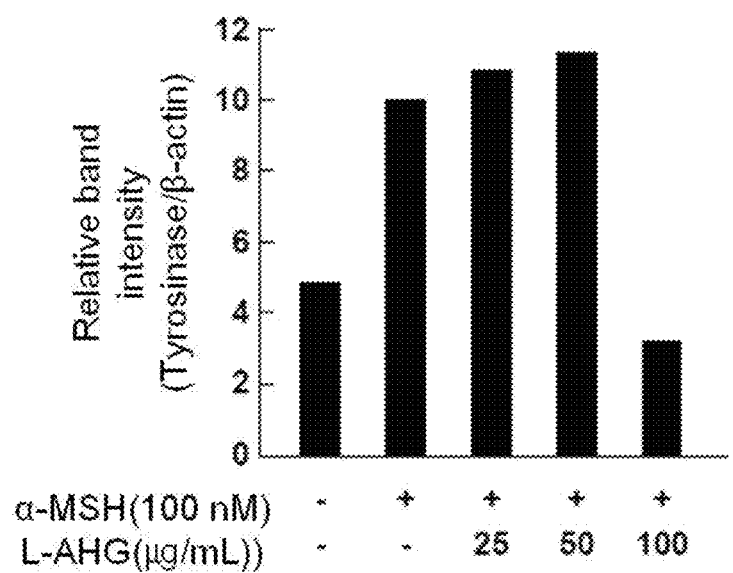
FIG. 9B shows a graph obtained by plotting the results of FIG. 9A as relative intensity of tyrosinase to β-actin.

As shown in FIGS. 9A and 9B, it was revealed that the tyrosinase expression induced by α-MSH significantly decreased in the HEMs when the HEMs were treated with 100 μg/mL of L-AHG, compared to the tyrosinase expression induced by α-MSH.

Figure 10A:
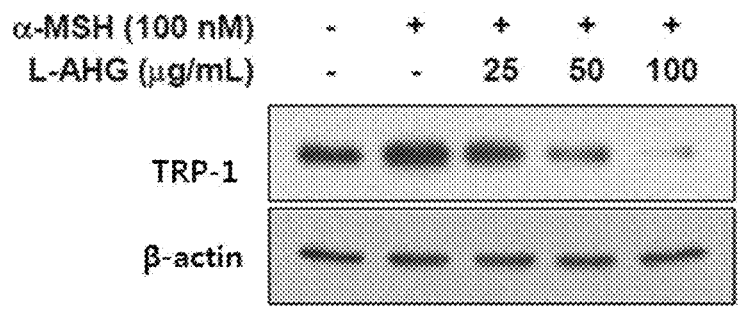
FIG. 10A shows the results of TRP-1 expression in the cells exposed to α-MSH after treatment according to concentrations of L-AHG
Figure 10B:
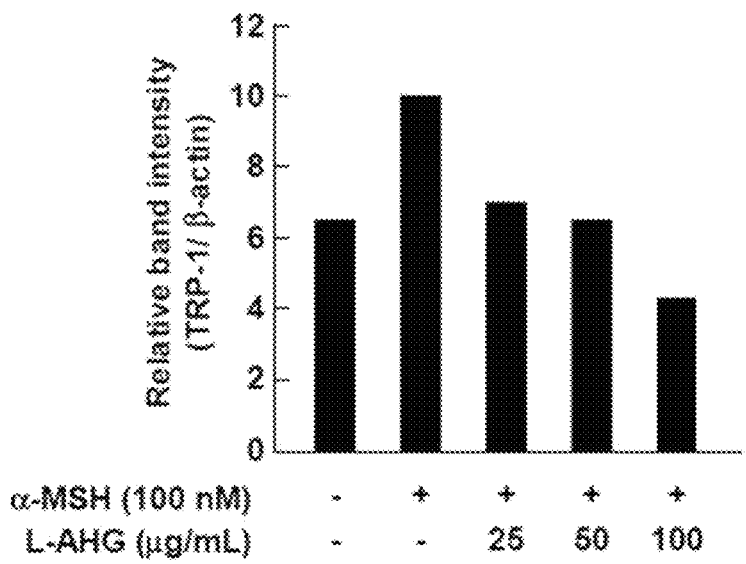
FIG. 10B shows a graph obtained by plotting the results of FIG. 10A as relative intensity of TRP-1 to β-actin.

Also, it was confirmed that, similar to the decrease in the tyrosinase expression by L-AHG treatment (FIG. 9A), the TRP-1 expression in the HEMs decreased in an L-AHG concentration-dependent manner (FIGS. 10A and 10B).

Figure 11:
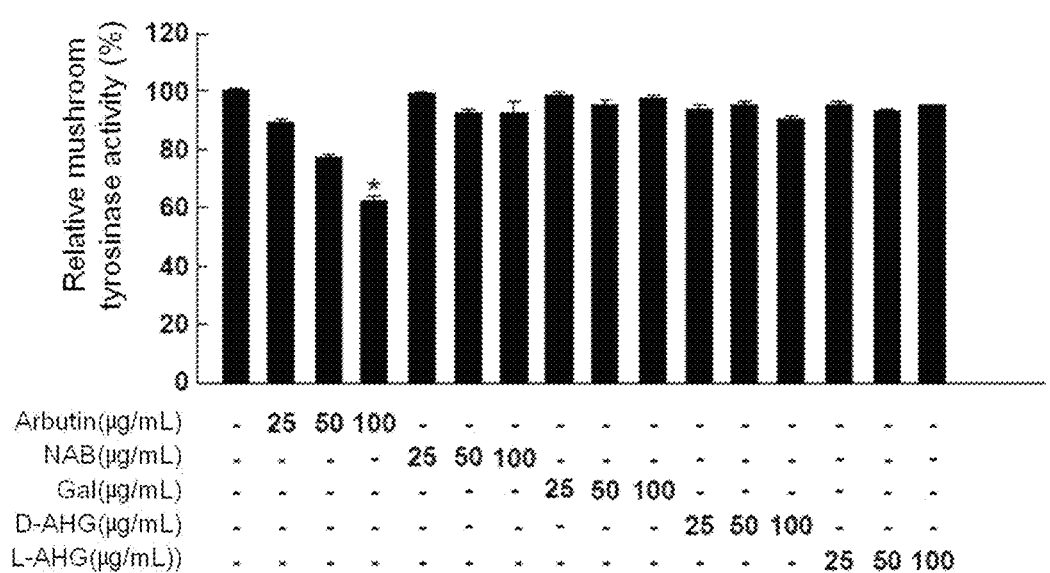
FIG. 11 shows effects of L-AHG on in vitro tyrosinase activities.

Next, effects of L-AHG on the tyrosinase activities were examined using a cell-free assay system. Many reports disclosed that the mushroom-derived tyrosinase was primarily used as a model since it was able to be used in the form of a tablet. Arbutin that was a competitive inhibitor of L-tyrosine was used as the positive control, and inhibited the tyrosinase activities in the mushroom (FIG. 11). The results were represented by the relative tyrosinase activities to the non-treated control. The data represented the average values±S.D. obtained from the independent experiments performed in triplicate, and the student's t-test was used for single statistical comparison. A significance value of p<0.05 was used as the standard to the statistical significance. An asterisk represents a significant difference (p<0.05) compared to the non-treated control.

As shown in FIG. 11, it was revealed that L-AHG did induce no significant decrease in the tyrosinase activities in the mushroom, and that arbutin induced a decrease in the tyrosinase activities to 40% at a concentration of 200 μM.

In sum, the results addressed that L-AHG was a novel hypopigmenting agent inhibiting the expression of tyrosinase and TRP-1.

<Example 9> Experiment of Moisturizing Effect of 3,6-Anhydro-L-Galactose in Human Corneous Cells Hyaluronan (HA) is a glycosaminoglycan composed of D-glucuronic acid and N-acetyl-D-glucosamine. Due to its capability to store a large amount of water, HA functions to play an important role in regulating the water balance and osmotic pressure. HA is synthesized by HASs 1, 2, and 3 in a cell membrane. In particular, HAS2 is found in normal human tissues. The previous studies showed that the genetic defect of HAS2 induced the fatality in the prenatal period in a mouse model, and the HAS2 gene was expressed in the epidermis and the derma of an adult human skin to a decreased level. Therefore, an increase in the HAS2 expression could be a good strategy for maintaining the homeostasis in the skin. To measure an induction time and concentration of L-AHG for HAS2 expression, a western blot assay was performed. The cells used for this purpose were HaCaT cells, and incubated at 37° C. under a 5% CO$_2$ atmosphere in a Dulbecco's modified Eagle's medium (DMEM, GIBCO Invitrogen, Auckland, NZ) supplemented with 10% FBS and penicillin/streptomycin.

The cells (1×10$^5$) were incubated for 24 hours in a 6-cm dish, and fasted in a serum-free medium for another 24 hours to get rid of an effect of FBS on activation of kinases. Thereafter, the cells were treated with 3,6-anhydro-L-galactose (L-AHG) at a predetermined concentration for a predetermined period of time. Then, the cells were lysed in a lysis buffer [20 mM Tris-HCl (pH 7.5), 150 mM NaCl, 1 mM Na$_2$EDTA, 1 mM EGTA, 1% Triton X-100, 2.5 mM sodium pyrophosphate, 1 mM β-glycerophosphate, 1 mM Na$_3$VO$_4$, 1 g/mL leupeptin, 1 mM phenylmethylsulfonyl fluoride (PMSF), and a protease inhibitor cocktail tablet]. The concentration of the proteins was measured according to the manufacturer's manual using a dye-conjugated protein assay kit (Bio-Rad Laboratories Inc). 10% SDS-PAGE was performed on the lysed proteins (20 to 40 μg), and the lysed proteins were transferred to a PVDF membrane through electrophoresis (Millipore Corp., Bedford, Mass., USA). After blotting, the membrane was blocked with 5% skim milk for 2 hours, and incubated with a primary antibody (goat anti-mouse IgG-HRP) overnight at 4° C. Thereafter, the membrane was incubated with a secondary antibody (a goat anti-rabbit IgG HRP-conjugated secondary antibody), and the antibody-bound proteins were detected using a chemifluorescence detection kit (Amersham Pharmacia Biotech, Piscataway, N.J.). The data represented the values obtained from the independent experiments performed in duplicate.

Figure 12A:
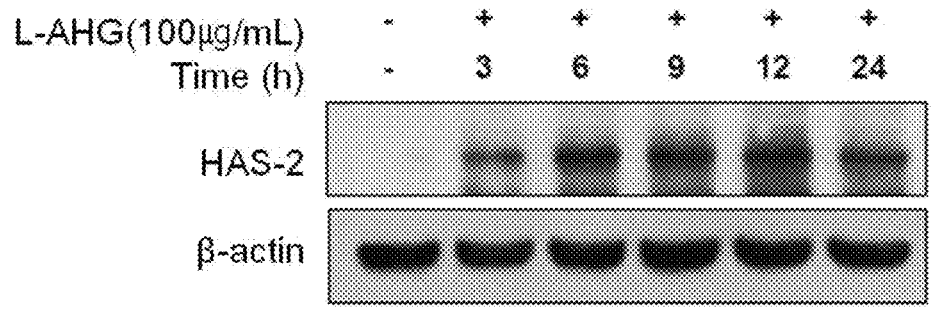
FIG. 12A shows an expression level of HAS2 after treatment with 100 μg/mL of L-AHG according to the elapse of time.
Figure 12B:
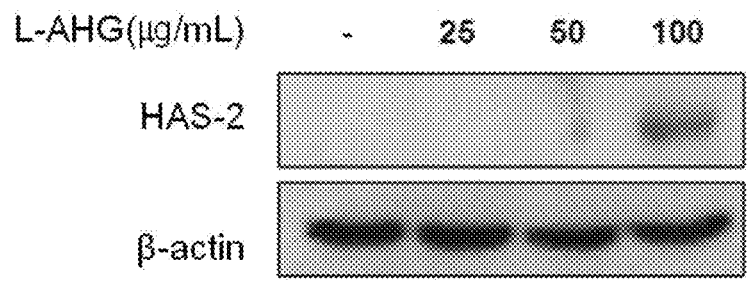
FIG. 12B shows an expression level of HAS2 after treatment according to concentrations of L-AHG

As shown in FIGS. 12A and 12B, it was revealed that L-AHG increased the HAS2 expression at 3 hours after the treatment. Also, it was confirmed that L-AHG increased the HAS2 expression in a concentration-dependent manner.

It was reported that the HAS2 expression was regulated by various inflammatory signal transduction pathways such as MAPKs and AKT. Therefore, the effects of L-AHG in the various inflammatory signal transduction pathways were measured.

Figure 13A:
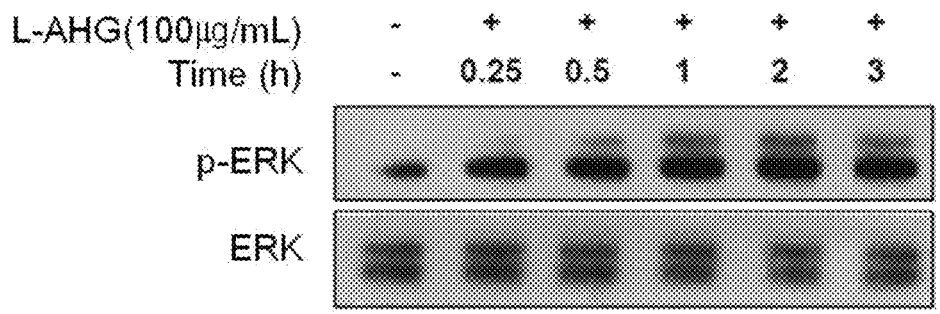
FIG. 13A shows the ERK phosphorylation results after treatment with 100 μg/mL of L-AHG according to the elapse of time.
Figure 13B:
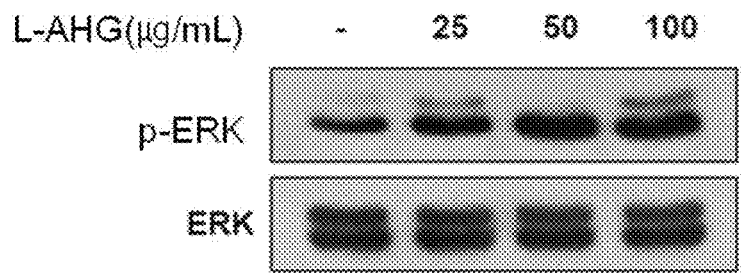
FIG. 13B shows the ERK phosphorylation results after treatment according to concentrations of L-AHG

As shown in FIG. 13A, it was revealed that 100 μg/mL of L-AHG significantly increased the phosphorylation of ERK 3 hours after the treatment. To measure a concentration-dependent effect of L-AHG on the phosphorylation of ERK, the cells were treated with L-AHG at concentrations of 25, 50, and 100 μg/mL. Similar to the HAS2 expression induced by L-AHG (FIG. 13B), it was revealed that the phosphorylation of ERK increased in an L-AHG concentration-dependent manner.

Figure 14A:
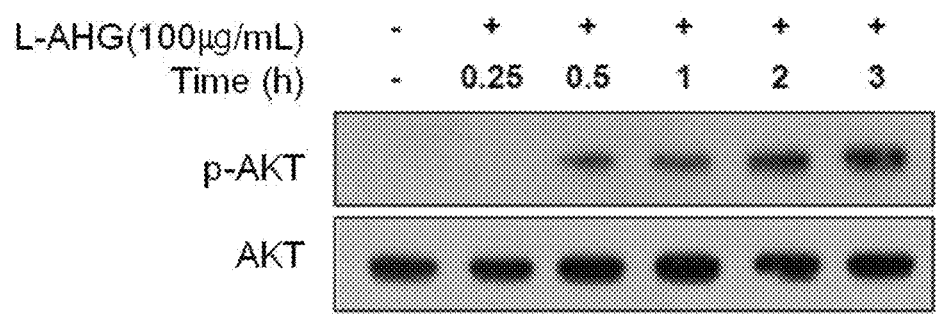
FIG. 14A shows the AKT phosphorylation results after treatment with 100 μg/mL of L-AHG according to the elapse of time.
Figure 14B:
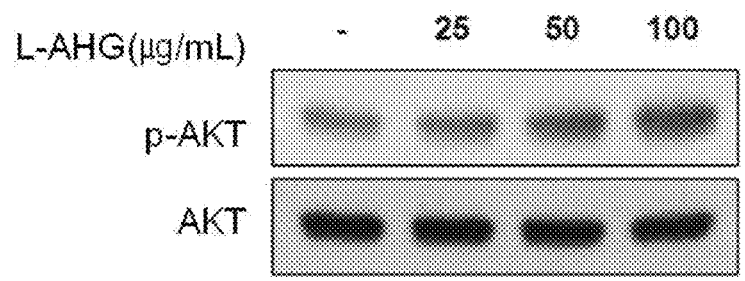
FIG. 14B shows the AKT phosphorylation results after treatment according to concentrations of L-AHG

As shown in FIG. 14A, it was revealed that 100 μg/mL of L-AHG significantly increased the phosphorylation of AKT 3 hours after the treatment. To measure a concentration-dependent effect of L-AHG on the phosphorylation of AKT, the cells were treated with L-AHG at concentrations of 25, 50, and 100 μg/mL. And, it was revealed that L-AHG increased the phosphorylation of AKT in a concentration-dependent manner (FIG. 14B).

In summary, the results addressed that the phosphorylation of ERK and AKT induced by L-AHG contributed to an increase in the HAS2 expression by L-AHG According to exemplary embodiments of the present invention, a monosaccharide, 3,6-anhydro-L-galactose, can be produced with a high yield by preparing an oligosaccharide under a mild chemical treatment condition in which an over-degradation effect according to chemical treatment is minimized and subjecting the oligosaccharide to enzymatic treatment.

Also, according to the present invention, the physiological activities of 3,6-anhydro-L-galactose, such as whitening, moisturizing, antioxidant, and antiinflammatory activities, are first examined, resulting in use in various fields including foods, cosmetics, medicine, and the like. Therefore, the 3,6-anhydro-L-galactose considered to be a by-product or a fermentation inhibitor upon production of red alga-derived bioenergy can be applied to production of higher value-added materials in the field of bioenergy.

According to exemplary embodiments of the present invention, 3,6-anhydro-L-galactose can be used as a whitening agent, a moisturizing agent, an antioxidant, a hypopigmenting agent, or an antiinflammatory agent.

What is claimed is:

1. A method for treating inflammatory diseases, comprising administering an effective amount of 3,6-anhydro-L-galactose to a subject in need thereof.

2. The method of claim 1, wherein the subject is a dog, a cat, a mouse, or a human.

* * * * *

SEQUENCE LISTING

<160> NUMBER OF SEQ ID NOS: 4

<210> SEQ ID NO 1
<211> LENGTH: 747
<212> TYPE: PRT
<213> ORGANISM: Saccharophagus degradans 2-40

<400> SEQUENCE: 1

```
Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr
        35                  40                  45

Thr Gly Leu Ala Ile Val Pro Glu Gln Pro Trp Asp Trp Ser Glu Phe
    50                  55                  60

Thr Ser Ala Ser Leu Tyr Phe Asp Ile Val Ser Val Gly Asp His Ser
65                  70                  75                  80

Thr Gln Phe Tyr Leu Asp Val Thr Asp Gln Asn Gly Ala Val Phe Thr
                85                  90                  95

Arg Ser Ile Asp Ile Pro Val Gly Lys Met Gln Ser Tyr Tyr Ala Lys
            100                 105                 110

Leu Ser Gly His Asp Leu Glu Val Pro Asp Ser Gly Asp Val Asn Asp
        115                 120                 125

Leu Asn Leu Ala Ser Gly Leu Arg Ser Asn Pro Pro Thr Trp Thr Ser
    130                 135                 140

Asp Asp Arg Gln Phe Val Trp Met Trp Gly Val Lys Asn Leu Asp Leu
145                 150                 155                 160

Ser Gly Ile Ala Lys Ile Ser Leu Ser Val Gln Ser Ala Met His Asp
                165                 170                 175

Lys Thr Val Ile Ile Asp Asn Ile Arg Ile Gln Pro Asn Pro Pro Gln
            180                 185                 190

Asp Glu Asn Phe Leu Val Gly Leu Val Asp Glu Phe Gly Gln Asn Ala
        195                 200                 205

Lys Val Asp Tyr Lys Gly Lys Ile His Ser Leu Glu Glu Leu His Ala
    210                 215                 220

Ala Arg Asp Val Glu Leu Ala Glu Leu Asp Gly Lys Pro Met Pro Ser
225                 230                 235                 240

Arg Ser Lys Phe Gly Gly Trp Leu Ala Gly Pro Lys Leu Lys Ala Thr
```

-continued

```
            245                 250                 255
Gly Tyr Phe Arg Thr Glu Lys Ile Asn Gly Lys Trp Met Leu Val Asp
                260                 265                 270
Pro Glu Gly Tyr Pro Tyr Phe Ala Thr Gly Leu Asp Ile Ile Arg Leu
            275                 280                 285
Ser Asn Ser Ser Thr Met Thr Gly Tyr Asp Tyr Asp Gln Ala Thr Val
            290                 295                 300
Ala Gln Arg Ser Ala Asp Asp Val Thr Pro Glu Asp Ser Lys Gly Leu
305                 310                 315                 320
Met Ala Val Ser Glu Lys Ser Phe Ala Thr Arg His Leu Ala Ser Pro
                325                 330                 335
Thr Arg Ala Ala Met Phe Asn Trp Leu Pro Asp Tyr Asp His Pro Leu
            340                 345                 350
Ala Asn His Tyr Asn Tyr Arg Arg Ser Ala His Ser Gly Pro Leu Lys
            355                 360                 365
Arg Gly Glu Ala Tyr Ser Phe Tyr Ser Ala Asn Leu Glu Arg Lys Tyr
            370                 375                 380
Gly Glu Thr Tyr Pro Gly Ser Tyr Leu Asp Lys Trp Arg Glu Val Thr
385                 390                 395                 400
Val Asp Arg Met Leu Asn Trp Gly Phe Thr Ser Leu Gly Asn Trp Thr
                405                 410                 415
Asp Pro Ala Tyr Tyr Asp Asn Asn Arg Ile Pro Phe Phe Ala Asn Gly
            420                 425                 430
Trp Val Ile Gly Asp Phe Lys Thr Val Ser Ser Gly Ala Asp Phe Trp
            435                 440                 445
Gly Ala Met Pro Asp Val Phe Asp Pro Glu Phe Lys Val Arg Ala Met
450                 455                 460
Glu Thr Ala Arg Val Val Ser Glu Glu Ile Lys Asn Ser Pro Trp Cys
465                 470                 475                 480
Val Gly Val Phe Ile Asp Asn Glu Lys Ser Phe Gly Arg Pro Asp Ser
                485                 490                 495
Asp Lys Ala Gln Tyr Gly Ile Pro Ile His Thr Leu Gly Arg Pro Ser
            500                 505                 510
Glu Gly Val Pro Thr Arg Gln Ala Phe Ser Lys Leu Leu Lys Ala Lys
            515                 520                 525
Tyr Lys Thr Ile Ala Ala Leu Asn Asn Ala Trp Gly Leu Lys Leu Ser
            530                 535                 540
Ser Trp Ala Glu Phe Asp Leu Gly Val Asp Val Lys Ala Leu Pro Val
545                 550                 555                 560
Thr Asp Thr Leu Arg Ala Asp Tyr Ser Met Leu Leu Ser Ala Tyr Ala
                565                 570                 575
Asp Gln Tyr Phe Lys Val Val His Gly Ala Val Glu His Tyr Met Pro
            580                 585                 590
Asn His Leu Tyr Leu Gly Ala Arg Phe Pro Asp Trp Gly Met Pro Met
            595                 600                 605
Glu Val Val Lys Ala Ala Ala Lys Tyr Ala Asp Val Val Ser Tyr Asn
            610                 615                 620
Ser Tyr Lys Glu Gly Leu Pro Lys Gln Lys Trp Ala Phe Leu Ala Glu
625                 630                 635                 640
Leu Asp Lys Pro Ser Ile Ile Gly Glu Phe His Ile Gly Ala Met Asp
                645                 650                 655
His Gly Ser Tyr His Pro Gly Leu Ile His Ala Ala Ser Gln Ala Asp
            660                 665                 670
```

Arg Gly Glu Met Tyr Lys Asp Tyr Met Gln Ser Val Ile Asp Asn Pro
            675                 680                 685

Tyr Phe Val Gly Ala His Trp Phe Gln Tyr Met Asp Ser Pro Leu Thr
        690                 695                 700

Gly Arg Ala Tyr Asp Gly Glu Asn Tyr Asn Val Gly Phe Val Asp Val
705                 710                 715                 720

Thr Asp Thr Pro Tyr Gln Glu Met Val Asp Ala Ala Lys Glu Val Asn
            725                 730                 735

Ala Lys Ile Tyr Thr Glu Arg Leu Gly Ser Lys
            740                 745

```
<210> SEQ ID NO 2
<211> LENGTH: 2244
<212> TYPE: DNA
<213> ORGANISM: Saccharophagus degradans 2-40

<400> SEQUENCE: 2
atgttattcg attttgaaaa cgatcaagtc ccttcaaata ttcattttt aaatgcgcgt      60 gcaagtatag aaacctatac cggtataaat ggcgagccga gtaaagggtt aaagttggcg    120
atgcagtcca agcagcacag ttatactggc cttgccattg tgccagagca gccttgggat    180
tggagcgagt ttacctctgc tagcttgtat ttcgatatag tcagtgttgg cgatcattcc    240 acacaattt atttagatgt taccgaccaa aatggcgccg tgtttacccg cagtattgat    300
attccagtgg gtaaaatgca atcgtactac gccaagttaa gcggtcacga tttagaagtg    360
cccgatagtg gagacgttaa cgatttaaac ctcgcctctg gcttgcgttc taacccgcct    420
acatggacat ctgacgatag gcagtttgtt tggatgtggg gagtgaaaaa tttagatttg    480
tcgggcattg ctaaaatatc gctaagtgtg caaagcgcaa tgcacgataa acagttatt    540 atcgataata ttcgtattca acccaacccg ccgcaagatg aaaacttcct tgtcggtttg    600
gtagacgagt ttggccaaaa cgccaaagtt gattacaagg gtaaaatcca tagtttagaa    660
gaattgcatg cagcgcgcga tgtggaactg gccgagcttg atggcaagcc aatgcctagt    720
cgctctaagt ttggcggttg gttggccggc ccaagctaa aagctacagg gtactttcgc    780
acagaaaaaa ttaacggtaa atggatgcta gtagacccag aagggtaccc ttactttgct    840
acgggtttag acattattcg cctatctaat tcatctacca tgactggtta cgattacgat    900
caagctactg ttgctcagcg ctctgccgac gatgtaacac ctgaagactc aaaaggttta    960
atggcagtga gcgaaaaatc atttgctacg cgccacctag catcgccaac cgagcggca   1020 atgtttaact ggttgccaga ttcgatcac cctctcgcaa atcattataa ctaccgtcgc   1080
tctgcgcatt ccggcccact gaaacgcggt gaagcctaca gcttctacag tgccaacctt   1140
gagcgtaaat acggtgaaac ttaccccggt tcttacttgg ataagtggcg cgaagtaacg   1200
gtagacagaa tgctaaactg gggctttacc tcgctaggca actggactga cccagcatat   1260
tacgacaaca atcgcatacc gttttcgcg aatggttggg taataggga ttttaaaacc   1320 gtatctagcg gtgcggatt ttggggcgca atgccagatg tattcgaccc agaatttaaa   1380
gtgcgcgcta tggaaacggc acgcgtggtt cagaagaaa ttaaaaatag cccttggtgc   1440
gtaggggtat ttatcgataa cgaaaaaagc ttcggtcgcc ccgattccga taaggcgcaa   1500
tacggtattc ccattcatac cctcggtcgc ccaagcgaag gtgtgcctac taggcaggcg   1560
tttagtaagc tgcttaaagc caaatacaaa actatagccg cgttaaacaa tgcctggggg   1620
ttaaagctta gttcttgggc tgagtttgat ttgggcgtag atgtaaaagc gctgccggta   1680
```

```
accgatactc tgcgcgcaga ttactcaatg ttactttcgg cctatgcgga ccaatatttt    1740
aaggtggtac acggcgcggt tgaacattac atgccgaacc acttgtattt aggcgcacgc    1800
tttcctgatt ggggaatgcc aatggaggta gtgaaagctg ccgcaaaata cgccgatgtg    1860
gttagctata attcctacaa agagggcttg cctaagcaga agtgggcttt tttagcagag    1920
ctagataagc cgagtataat cggtgagttt cacataggtg ctatggatca cggttcgtat    1980
caccccggtt taattcacgc tgcgtcgcag gccgatagag gtgaaatgta caaagattat    2040
atgcaatcgg taattgataa ccccctacttc gtaggcgcgc actggttcca gtatatggat    2100
tcgccattaa cgggcagagc ttatgatggt gaaaactaca atgtgggttt tgtggatgtt    2160
accgacacgc cgtaccaaga aatggtggat gcagcaaaag aagtaaatgc gaaaatatac    2220
accgaaaggc taggcagcaa ataa                                           2244
```

```
<210> SEQ ID NO 3
<211> LENGTH: 368
<212> TYPE: PRT
<213> ORGANISM: Saccharophagus degradans 2-40

<400> SEQUENCE: 3

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
        35                  40                  45

Ile Arg Arg Asp Pro Ser Ala Val Leu Lys Val Asp Asp Glu Tyr His
    50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
                85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
    130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
    210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
            260                 265                 270
```

Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
    290                 295                 300

Lys Gly Ala Pro Glu Ala Val Gly Phe Phe Arg Pro Glu Ser Asp Ser
305                 310                 315                 320

Asp Asp Pro Ile Ser Gly Ile Glu Trp Gly Leu Ser His Lys Tyr Asp
                325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
        355                 360                 365

<210> SEQ ID NO 4
<211> LENGTH: 1107
<212> TYPE: DNA
<213> ORGANISM: Saccharophagus degradans 2-40

<400> SEQUENCE: 4
atgagcgatt caaaagtaaa taaaaaattg agtaaagcta gcctgcgagc catagagcgc      60
ggctacgatg aaaaggggcc tgaatggctg tttgagtttg atattacccc actaaaaggc     120
gacttagcct acgaagaagg cgtaattcgt cgagacccca gcgcagtatt aaaggtggac     180
gatgaatatc acgtttggta caccaagggc gaaggtgaaa cagtaggctt cggcagcgac     240
aaccccgaag acaaagtctt cccatgggat aaaacagaag tttggcacgc cacctctaaa     300
gataagatta cttggaaaga aattggccct gccatacaac gcggcgcagc tggggcatat     360
gatgaccgtg cagtgttcac ccccgaagtc ctgcgccata acggcaccta ctaccttgta     420
tatcaaacgg taaagcgcc ctacttaaac cgatcgctag agcatatagc catcgcatac      480
agcgattccc cctttggccc atggaccaaa tccgatgcgc caattttaag cccagaaaat     540
gacggcgttt gggatacgga cgaagacaat cgatttttag taaaagagaa aggcagtttc     600
gatagccaca aagtcacga ccctgctta atgttttta caatcgttt ctacctgtat         660
tacaaaggcg agactatggg cgaaagcatg aacatgggcg gcagagaaat aaaacacggt     720
gtagccattg ccgactcgcc acttgggccc tacaccaaaa gcgaatacaa ccctattacc     780
aatagtggcc atgaagttgc cgtatggccc tacaaaggtg gaatggccac catgctaacc     840
accgacgggc cagaaaaaaa cacctgccag tgggcagaag acggcattaa ctttgacatt     900
atgtcgcata taaaaggcgc accagaagca gtaggttttt ttagaccaga aagcgatagc     960
gacgacccta agcggcat tgaatggggg ctaagccaca gtacgacgc cagctggaac       1020
tggaactatc tatgcttttt taaaacgcgt cgacaagttt tagatgcagg tagctatcag    1080
caaacaggcg attccggagc agtataa                                        1107